(12) United States Patent
Van Putten et al.

(10) Patent No.: US 12,222,556 B2
(45) Date of Patent: Feb. 11, 2025

(54) METHOD OF RE-CONNECTING OPTICAL FIBERS AND SYSTEM

(71) Applicant: KONINKLIJKE PHILIPS N.V., Eindhoven (NL)

(72) Inventors: Elbert Gerjan Van Putten, 'S-Hertogenbosch (NL); Adrianus Johannes Gerardus Mank, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 92 days.

(21) Appl. No.: 18/033,833

(22) PCT Filed: Oct. 27, 2021

(86) PCT No.: PCT/EP2021/079862
§ 371 (c)(1),
(2) Date: Apr. 26, 2023

(87) PCT Pub. No.: WO2022/096345
PCT Pub. Date: May 12, 2022

(65) Prior Publication Data
US 2023/0400643 A1 Dec. 14, 2023

(30) Foreign Application Priority Data
Nov. 6, 2020 (EP) .................... 20206132

(51) Int. Cl.
*G02B 6/38* (2006.01)
*A61B 5/06* (2006.01)
(Continued)

(52) U.S. Cl.
CPC .... *G02B 6/3843* (2013.01); *A61B 2034/2061* (2016.02); *A61B 2562/0266* (2013.01);
(Continued)

(58) Field of Classification Search
CPC ............ A61B 2034/2061; A61B 5/065; A61B 2562/0266; A61B 2562/227;
(Continued)

(56) References Cited

U.S. PATENT DOCUMENTS 8,773,650 B2 * 7/2014 Froggatt ............ G01M 11/3181
356/73.1
9,625,656 B2 * 4/2017 Sasaki .................... G02B 6/245
(Continued)

FOREIGN PATENT DOCUMENTS

WO 2017182535 A1 10/2017

OTHER PUBLICATIONS

Marcuse, "Loss Analysis of Single-Mode Fiber Splices", The Bell System Technical Journal, vol. 56, No. 5, May-Jun. 1977, pp. 703-718.
(Continued)

*Primary Examiner* — Ryan A Lepisto
*Assistant Examiner* — Erin D Chiem

(57) ABSTRACT

The present invention relates to a method of re-connecting a first optical fiber (12) with a second optical fiber (34), the first fiber (12) and the second fiber (34) each having a plurality of outer cores, comprising: (a) positioning a first end section of the first fiber (12) and a second end section of the second fiber (34) in proximity so as to be aligned with one another along a longitudinal axis of the first and second end sections in a current connection position including a current connection orientation, in which a current relative rotational angle between the first and second end sections about the longitudinal axis is not known with respect to a relative rotational angle between the first and second end sections in a registered connection orientation determined with respect to a coordinate system during a previous connection of the first fiber (12) with the second fiber (34);
(Continued)

(b) optically interrogating the outer cores of the first and second fibers (12, 34) through the current connection position to receive optical signals from the outer cores; (c) modifying, from the optical interrogation of the outer cores, the registered connection orientation such that the first and second fibers in the current connection orientation including the current relative rotational angle between the first and second end sections about the longitudinal axis are correctly registered with respect to the coordinate system.

15 Claims, 10 Drawing Sheets

(51) Int. Cl.
*A61B 34/20* (2016.01)
*G01B 11/16* (2006.01)
*G01D 5/353* (2006.01)
*G01M 11/00* (2006.01)
*G02B 6/02* (2006.01)

(52) U.S. Cl.
CPC .......... *G01B 11/161* (2013.01); *G01D 5/3538* (2013.01); *G01M 11/3181* (2013.01)

(58) Field of Classification Search
CPC ............... G01B 11/161; G01D 5/3538; G01D 5/35316; G01M 11/3181; G01M 11/3172
See application file for complete search history.

(56) References Cited

U.S. PATENT DOCUMENTS

| | | | |
|---|---|---|---|
| 9,759,873 B2 * | 9/2017 | Nakanishi | G02B 6/3843 |
| 10,416,391 B2 * | 9/2019 | Froggatt | G01M 11/3172 |
| 10,551,170 B2 * | 2/2020 | 'T Hooft | A61B 1/009 |
| 10,663,290 B1 * | 5/2020 | Tongue | G01B 11/245 |
| 10,739,529 B2 | 8/2020 | Froggatt et al. | |
| 10,775,157 B2 * | 9/2020 | Gifford | G01D 18/00 |
| 11,079,217 B2 | 8/2021 | Van Putten et al. | |
| 2011/0113852 A1 * | 5/2011 | Prisco | A61B 34/30 |
| | | | 385/13 |
| 2017/0265840 A1 | 9/2017 | Bharat et al. | |
| 2017/0290563 A1 | 10/2017 | Cole et al. | |
| 2018/0017920 A1 | 1/2018 | Aiba | |
| 2019/0391341 A1 | 12/2019 | Froggatt et al. | |

OTHER PUBLICATIONS

International Search report and Written Opinion of PCT/EP2021/079862, dated Jan. 17, 2022.

* cited by examiner a) Conventional setup b) Setup A suitable for backloadable FORS guidewires c) Setup B suitable for backloadable FORS guidewires

METHOD OF RE-CONNECTING OPTICAL FIBERS AND SYSTEM

CROSS-REFERENCE TO PRIOR APPLICATIONS

This application is the U.S. National Phase application under 35 U.S.C. § 371 of International Application No. PCT/EP2021/079862, filed on Oct. 27, 2021, which claims the benefit of European Patent Application No. 20206132.1, filed on Nov. 6, 2020. These applications are hereby incorporated by reference herein.

FIELD OF THE INVENTION

The present invention generally relates to the field of optical shape sensing (OSS) using optical fiber sensors, also referred to as FORS (Fiber Optic Real Shape). In particular, the present invention relates to a method of re-connecting optical fibers with one another. Re-connecting optical fibers may be necessary in a procedure in which FORS is used. The present invention further relates to a system used for reconstructing shape of a fiber sensor.

BACKGROUND OF THE INVENTION

While the present description refers to the use of FORS in the medical or surgical field, it is to be understood that the invention is not limited thereto.

In the medical field, there is a clear and ongoing trend to replace conventional surgical procedures with minimally invasive interventions. In these interventions, medical devices such as e.g. guidewires, catheters, endoscopes and needles are inserted into the body through small incisions thereby minimizing scaring and reducing complications and side effects for the patient. Physicians can use several visualization techniques to navigate these medical devices inside the body.

In many procedures, X-ray imaging is currently the golden standard to provide real-time monitoring of the devices. However, this imaging technique exposes the patient and the medical team to harmful ionizing radiation. Furthermore, it provides a solely 2-dimensional projection. This projection lacks critical information about the 3-dimensional shape of the medical instrument such as its direction and orientation with respect to the anatomy of the patient. Additional information about the shape of a device would help the physician tremendously in navigating through the body and could reduce procedure times.

There are several non-imaging tracking technologies that can determine the position and the orientation of devices. Such tracking systems can be based on sensing with electromagnetic, acoustic, impedance, and optical technologies and may use principles such as signal strength (and attenuation), signal phase/frequency shifts, and/or time-of-flight to triangulate a sensor in 3-dimensional space.

Fiber Optic Real Shape (FORS) is one of these tracking technologies. In FORS, geometrical changes of the device are encoded into the light field that propagates through a special type of optical fiber integrated in the device. Optical interrogation of this fiber gives the information needed to, in principle, reconstruct the 3-dimensional shape of the whole optical fiber (and hence that of the device), in real time. Given an appropriate reference frame (coordinate system), one now knows the exact orientation and position of the complete medical device in real time.

The optical fiber that is being used to determine the shape of the device (FORS sensor) typically comprises multiple optical cores, for example a central core and multiple outer cores that may spiral around the central core along the length of the optical fiber. For example, an optical fiber may comprise four cores, one central core and three outer cores that may be located at nominally 120° from each other at a fixed distance from the central core. For the present invention, the number of outer cores should be equal to or more than two.

To make a functional connection between a first optical fiber, for example an optical fiber integrated into a medical device, and a second optical fiber, for example an optical fiber integrated into a patch cord connected to the optical interrogator, it is important to align the outer cores of both fibers. A common way to achieve such an alignment is to assemble both fibers into a fiber connector and mate them in a mating sleeve. Low tolerance elements in the connector, such as ceramic ferrules, ensure the centering of the two fibers inside a mating sleeve. The connector key defines the angular alignment between the two optical fibers.

For certain designs of medical devices, for example guidewires, in particular back-loadable guidewires, where the outer diameter typically cannot be larger than a fraction of a millimeter, a robust connector key is difficult to manufacture. In that case, alternative alignment methods are needed to ensure a properly aligned connection between the outer cores of the two optical fibers.

In FORS, the reconstructed shape of the fiber sensor (hence of the medical device into which the fiber sensor is integrated) is typically displayed in a relevant coordinate system, such as one that matches an operating theatre in which FORS is used, for example a coordinate system which is linked to a fixed surgery table, or an X-ray system. To this end, a FORS sensor is typically registered to the relevant coordinate system during setup using e.g. one or more X-ray images. This registration can be a tedious process which is time-consuming. Thus, it is desirable to keep this registration once done during the entire surgical procedure. However, during a medical procedure, FORS guidewires might need to be disconnected from and re-connected to the optical interrogator several times. This especially holds for back-loadable FORS guidewires for which the conventional way of fixating the launch position (the position of the fiber sensor where shape reconstruction starts) cannot be used because there are strict restrictions on the outer diameter of the medical device. When such a device, e.g. a guidewire, is disconnected to slide a therapy device over the proximal end of the guidewire, it is not desirable to need a re-registration after the re-connect of the fiber sensor to the optical patch cord connected with the interrogator as this would cause delay in the procedure.

Upon re-connecting the two optical fibers, for example the optical fiber integrated in the device and the optical fiber integrated into the patch cord, the cores of the two optical fibers need to be aligned with high accuracy. It is known to measure reflectivity to ensure such a good alignment, as described in US 2019/0391341 A1. It is also known to use a recalibratable/reassignable calibration data set for each outer core to ensure a good re-connection, involving a comparison of the measured optical response of the respective interrogated fiber core with the calibration data sets of the respective fiber core of the patch cord, as disclosed in WO 2017/182535 A1.

Nevertheless, there is still a need in a method which assists a user in re-connecting two optical fibers, minimizes the amount of required registration steps and improves the work flow in, for example, an operating theatre.

SUMMARY OF THE INVENTION

It is an object of the invention to provide an improved method of re-connecting a first optical fiber with a second optical fiber.

It is a further object of the present invention to provide a method of re-connecting optical fibers to one another which does not require a re-registration of the fibers in a relevant coordinate system.

It is a further object of the present invention to provide a method of re-connecting optical fibers which is highly suitable for back-loadable guidewires having an optical fiber integrated therewith.

It is a further object of the present invention to provide a system which may make use of the method according to the invention.

According to a first aspect of the invention, a method of re-connecting a first optical fiber with a second optical fiber is provided, the first fiber and the second fiber each having a plurality of outer cores, the method comprising:

(a) positioning a first end section of the first fiber and a second end section of the second fiber in proximity so as to be aligned with one another along a longitudinal axis of the first and second end sections in a current connection position including a current connection orientation in which a current relative rotational angle between the first and second end sections about the longitudinal axis is not known with respect to a relative rotational angle between the first and second end sections in a registered connection position including a registered connection orientation which has been determined with respect to a coordinate system during a previous connection of the first fiber with the second fiber, (b) optically interrogating the outer cores of the first and second fibers through the current connection position to receive optical signals from the outer cores, (c) modifying, from the optical interrogation of the outer cores, the registered connection orientation such that the first and second fibers in the current connection orientation including the current relative rotational angle between the first and second end sections about the longitudinal axis are correctly registered with respect to the coordinate system.

The method according to the invention facilitates a re-connect of two optical fibers. In particular, the method according to the invention eliminates the need for re-registration of the fibers with respect to the relevant coordinate system. When re-connecting the first fiber with the second fiber, mutual end sections of the first and second fibers are positioned in proximity to each other. While position of the fibers along the longitudinal axis and in two directions perpendicular to the longitudinal axis and orientation about two axes perpendicular to the longitudinal axis may be defined mechanically with high precision, the remaining degree of freedom, namely the current relative rotational angle between the first and second end sections about the longitudinal axis is not known, at least not with the necessary accuracy. The method according to the invention allows determining the relative rotational angle between the first and second end sections in the current connection orientation by optically interrogating the outer cores of the first and second fibers through the current connection position to receive optical signals from the outer cores. Thus, the method according to the invention makes use of an optical measurement of the two fibers through the current connection position. The result of this measurement is then used to modify the registered connection orientation which has been previously determined, for example during setup of the system, with respect to a coordinate system upon a previous connection of the fibers, such that the first and second fibers in the current connection orientation including the current relative rotational angle between the first and second end sections about the longitudinal axis are correctly registered with respect to this coordinate system. During optical interrogation of the outer cores of the first and second fibers, the two fibers may be rotated with respect to one another (for example by rotating the distal fiber with respect to the proximal fiber) until the optical signals received from the outer cores are optimum. However, such a rotation will typically not be so exact that the relative rotational angle between the fiber end sections will be the same as in the previous connection which was the basis of the registration. Performing an optical measurement through optically interrogating the outer cores of the two fibers allows to obtain much more precise results from which the relative rotational angle between the end sections of the two fibers may be derived. These measurement results can now be used to modify the registered connection orientation of the two fibers about the longitudinal axis which has been obtained from a previous connection and registration with the relevant coordinate system. In a subsequent shape reconstruction process, the previous, for example initial, registration can be further used, but which is now corrected with the current actual relative rotational angle obtained from the optical interrogation. This eliminates the need for a re-registration of the fibers in the relevant coordinate system.

For the implementation of the method according to the present invention, there is no need to use a connector having a connector key to define the rotational alignment of the two fibers about the longitudinal axis. Hence, the method according to the invention is highly suitable for back-loadable guidewires having an optical fiber integrated therewith.

Preferred embodiments of the invention are defined in the dependent claims and as described in the present disclosure.

In an embodiment, the method may further comprise indicating to a user a direction in which the first and second end sections are to be rotated with respect to one another about the longitudinal axis for increasing intensity of the received signals to an optimum.

When the user tries to refine the relative rotational position of the two fibers about the longitudinal axis to get a better signal, he or she does not know on which side of the optimum the current alignment is. By indicating the user the direction in which the first and second sections are to be rotated with respect to one another about the longitudinal axis in contrast enables a more intuitive and therefore faster feedback for aligning the outer cores during re-connection compared to simply looking at the strength of signal as function of orientation. Thus, faster alignment may be achieved which is advantageous in view of the duration of an intervention and the number of device exchanges needed for a complex procedure.

The indication may be provided to the user as a visual indication on a display or graphical user interface. The indication may also be provided as an acoustic indication, for example a sound with varying loudness or varying frequency indicating the direction into which the fibers are to be rotated relative to one another.

It is to be understood that a rotation of the first and second end sections with respect to one another includes rotating the first end section only, rotating the second end section only, and rotating both the first and second end sections.

In an embodiment, step (c) may comprise determining, from the optical interrogation of the outer cores, the current relative rotational angle between the first and second end sections and correcting the registered connection orientation with the determined current relative rotational angle.

With the optical measurement result obtained from the optical interrogation of the outer cores of the two fibers, the current relative rotational angle between the end sections of the fibers can be determined very accurately. Knowing the current relative rotational angle simplifies the modification of the registered connection orientation. Modification may be performed by using the difference of the current rotational angle and the rotational angle in the previous connection.

In an embodiment, step (b) may include deriving, from the optical signals, an optical quantity chosen from the group consisting of insertion loss, transmission, reflection, at the current connection position for each of the outer cores.

The optical quantities indicated above can be measured, from the optical interrogation of the outer cores of the fiber, with very high accuracy. Insertion loss is a measure of the loss of the optical signal power at the connection position and may be expressed in dB (decibels). Insertion loss is related with the relative rotational angle between the first and second end sections about the longitudinal axis. From measuring insertion loss at the current connection position, the relative rotation angle can be determined in a simple manner, as will be described in more detail herein.

In connection with the previous embodiment, the method may further comprise determining, from the optical quantity for each core, the current relative rotational angle between the first and second end sections based on a stored characteristic specific of the two fibers to be re-connected.

Preferably, the stored characteristic may be obtained from an optical measurement of the optical quantity for a plurality of relative rotational angles between the first and second end sections during a previous connection of the first fiber with the second fiber.

During an initial (or previous) connection (and before registration), the two fibers may be rotated relative to each other, and the optical quantity, e.g. insertion loss, in the outer cores is continuously determined. Using these data points, the angular positions of the outer cores of the first fiber relative to the angular positions of the outer cores of the second fiber may be estimated, and these relative angular positions can be used as the stored characteristic. When the fibers are aligned well enough, the fibers can be left in that orientation and a registration step may then be performed. During a re-connection phase, the previously stored characteristic may be used and the optical quantity (e.g. insertion losses) is measured during the re-connection determine the relative orientation (relative rotational angle). One could even rotate the two fibers with respect to one another again during the re-connection phase and from that again determine the relative angular positions of the outer cores, or combine these measurements with the measurements during the initial connection to refine the relative angular positions.

Alternatively, the stored characteristic may be obtained from a measurement upfront as a manufacturing step of the fibers, e.g. a patch cord and a sensor equipped with the fibers.

In order to be able to use the previous, for example initial, registration of the fiber connection in the relevant coordinate system, it is important to know the current relative rotational angle at the current connection position relative to the previous connection position used for registration. Hence, basing the determination, for example calculation, of the current relative rotational angle on a stored characteristic obtained from a measurement of the (same) optical quantity during the previous connection of the fibers is perfectly tailored to the alignment of the fibers on which the (initial) registration was based.

Further, using a stored characteristic which is specific of the actual combination of two specific fibers reduces calculation time and expenditure in determining the current relative rotational angle in comparison with determining this characteristic anew during re-connection of the two fibers. Further, accuracy in determining the difference between the current alignment and the previous alignment is also increased.

The stored characteristic may include deviations of angular positions of the outer cores of the first fiber with respect to angular positions of the outer cores of the second fiber.

Such deviations of angular positions of the outer cores between the two fibers may be caused by tolerances in the process of manufacturing the optical fibers. These deviations are specific of the actual two fibers which are to be connected and re-connected in a procedure. Taking into account these deviations when determining the relative rotational angle between the fibers increases accuracy of the measurement of the optical quantity from which the relative rotational angle is determined.

When considering two optical fibers, each having a number N of outer cores, there are N possible combinations of core-to-core configurations upon re-connecting the two fibers. For example, if the two fibers each have three outer cores, there are three possible combinations of the outer cores of the first fiber with the outer cores of the second fiber. In a previous connection, the fibers were connected in one core-to-core configuration. When this core-to-core configuration is also used in the re-connection of the two fibers, then it is sufficient to know the deviations between the angular positions of the outer cores of the first fiber and the angular positions of the outer cores of the second fiber for this specific core-to-core configuration. Hence, computational expenditure and computation time may be reduced in this embodiment.

It is, however, also possible that the stored characteristic includes deviations between the angular positions of the outer cores of the first fiber and the angular positions of the outer cores of the second fiber for all possible combinations of the outer cores of the first fiber with the outer cores of the second fiber.

In this case, the stored characteristic includes N parameters. The advantage of this embodiment is that upon re-connecting the two fibers, it is not essential that the core-to-core configuration of the re-connection is the same as in the previous connection. Since the user does not have to take care that the same cores of the first fiber are aligned with the same cores as in the previous connection, re-connecting and alignment of the two fibers is further simplified.

In either of the two embodiments described before, it is advantageous if the method further comprises identifying the current combination of the outer cores of the first fiber with outer cores of the second fiber.

Identification of the current combination of the outer cores of the two fibers may be performed as described in WO 2017/182535 A1 which discloses to identify the core-to-core configuration by comparison of a measured optical response of an interrogated fiber core with calibration data sets of the respective core of the other fiber.

In an embodiment, the method may further comprise indicating to a user to rotate the first and second fibers relative to one another about the longitudinal axis until the same cores of the first and second fibers are optically connected with one another as in the previous connection of the first fiber with the second fiber.

This embodiment is advantageous in particular in context with the embodiment above, according to which the stored characteristic only includes deviations between the angular positions of the outer cores of the two fibers for that combination of the outer cores which have been in optical communication during the previous connection. Indicating the user how far to rotate the first and second fibers relative to one another about the longitudinal axis to come to the core-to-core configuration of the previous connection further assists the user in finding the "correct" (previous) core-to-core configuration as quickly as possible.

Again, the indication may be provided as a visual indication on a display or graphical user interface. The indication may also be provided as an acoustic indication, for example a sound with varying loudness or varying frequency indicating the direction into which the fibers are to be rotated relative to one another.

As mentioned above, if the stored characteristic includes the deviations between the angular positions of the outer cores of the two fibers for all possible combinations or core-to-core configurations, the user has not to take care to arrive at the core-to-core configuration of the previous connection, which also speeds up the alignment procedure, and further avoids large rotational movements of one or both of the two fibers and thus reduces the risk of wearing the connector used for connecting the two fibers.

In an embodiment, the registered connection position may be registered with respect to a launch position, and the second fiber is being connected with the first fiber directly at the launch position or in a distance distally from the launch position.

The launch position of an FORS system is the position where shape reconstruction of the FORS system starts. Conventionally, the launch position is mechanically fixed distally from any optical connection. In such a configuration, the fibers can be connected and disconnected while the launch position stays in a mechanical stable launch fixture. Such a configuration however, is not possible when a back-loadable guidewire integrated with a fiber is used. The present embodiment, where the connection between the two fibers is directly on the distal side of the launch position or in a distance distally from the launch position, instead enables use of a back-loadable guidewire. A further advantage of this embodiment is that the procedures of connecting, disconnecting, re-connecting the two fibers may be performed closer to the patient which is an improvement in a surgical procedure, in particular in complex surgical procedures in which connection, disconnection and re-connection have to be performed repeatedly.

In an embodiment, one of the first and second fibers is integrated in a device, and the method may further comprise reconstructing shape of the device using the registered position modified upon re-connection of the first and second fibers.

Re-registration of the device is not required as the registration performed in a previous connection of the two fibers can be further used after re-connection of the fibers, while the registration is modified by the current relative rotational angle between the two fibers. Integrated in a device includes the case where the fiber extends through an interior of the device, and also the case where the fiber extends along an outer side of the device.

According to a second aspect of the present invention, there is provided a system, comprising:
a first optical fiber and a second optical fiber, the first fiber and the second fiber each having a plurality of outer cores, a first end section of the first fiber and a second end section of the second fiber positioned with a first end section of the first fiber and a second end section of the second fiber aligned with one another along a longitudinal axis of the first and second end sections in a current connection position including a current connection orientation, in which a current relative rotational angle between the first and second end sections about the longitudinal axis is not known with respect to a relative rotational angle between the first and second end sections in a registered connection orientation which has been determined with respect to a coordinate system during a previous connection of the first fiber with the second fiber,
an optical interrogator configured to interrogate the outer cores of the first and second fibers through the current connection position to receive optical signals from the outer cores,
circuitry configured to modify, from the optical interrogation of the outer cores, the registered connection orientation such that the first and second fibers in the current connection orientation including the current relative rotational angle between the first and second end sections about the longitudinal axis are correctly registered with respect to the coordinate system.

In a further aspect of the present invention, there is provided a computer program comprising program code means for causing the system of the second aspect to carry out the steps of the method according to the first aspect.

It shall be understood that the claimed system and computer program have similar and/or identical preferred embodiments as the claimed method, in particular as defined in the dependent claims and as disclosed herein.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Before describing the invention in detail, some introductory explanations of FORS will be given which facilitate the understanding of the present invention.

Figure 1:
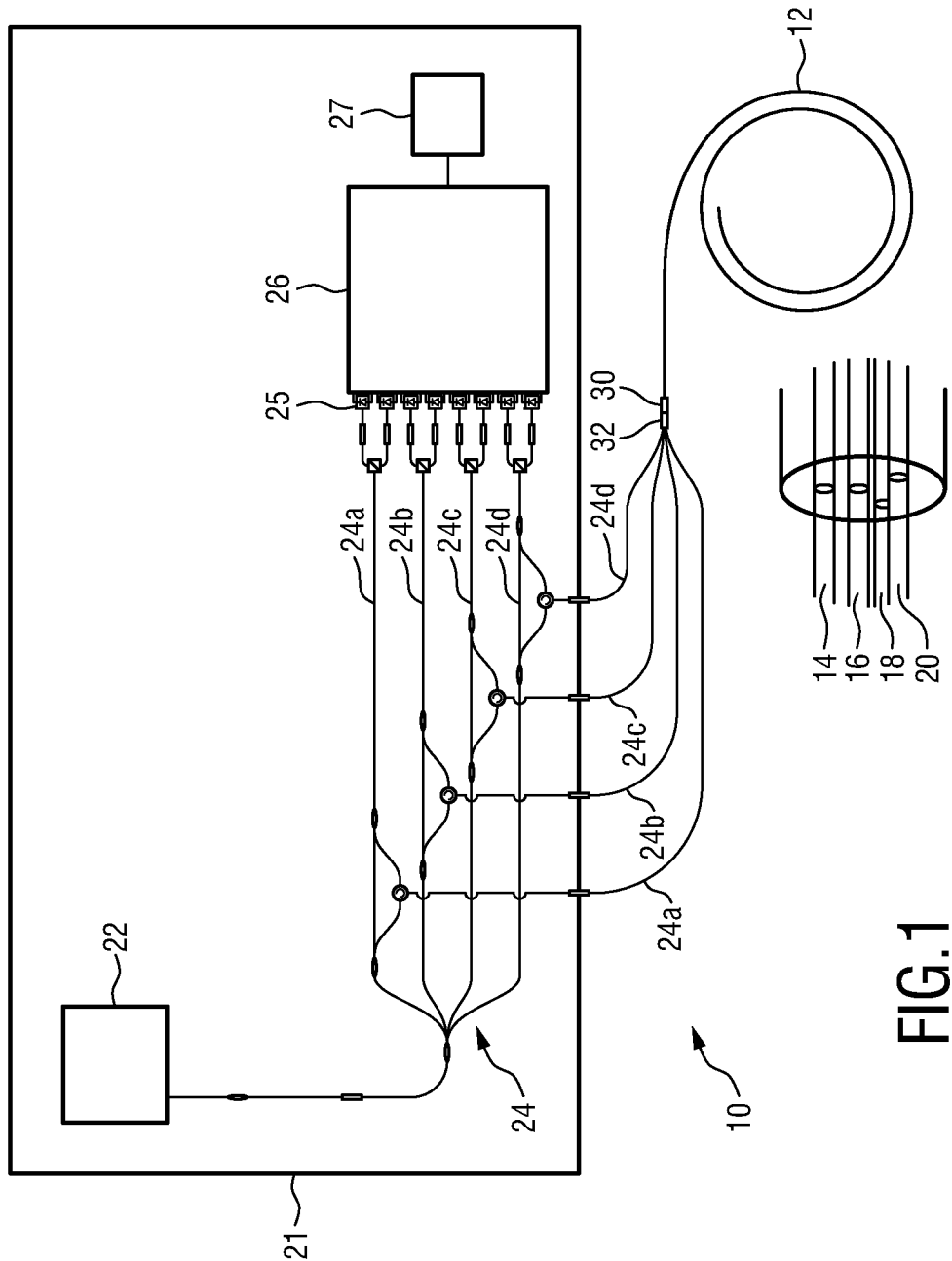
FIG. 1 shows an embodiment of a system suitable for FORS.

FIG. 1 schematically shows parts of a system 10 configured for sensing and reconstructing shape of an optical fiber sensor 12. System 10 may also be referred as FORS system 10.

The system 10 may be configured as a multi-channel Optical Frequency Domain Reflectometry (OFDR)-based and distributed-strain sensing system for interrogating the fiber sensor 12 and reconstructing shape of the optical fiber 12. The optical fiber 12 may have embedded therein a plurality of fiber cores 14, 16, 18, 20, in the present example four cores with one center core 16 and three outer cores 14, 18, 20. It shall be understood that the present invention is not limited to the use of a 4-core optical fiber, but can also be used for optical fibers having less or more than four cores.

Figure 2:
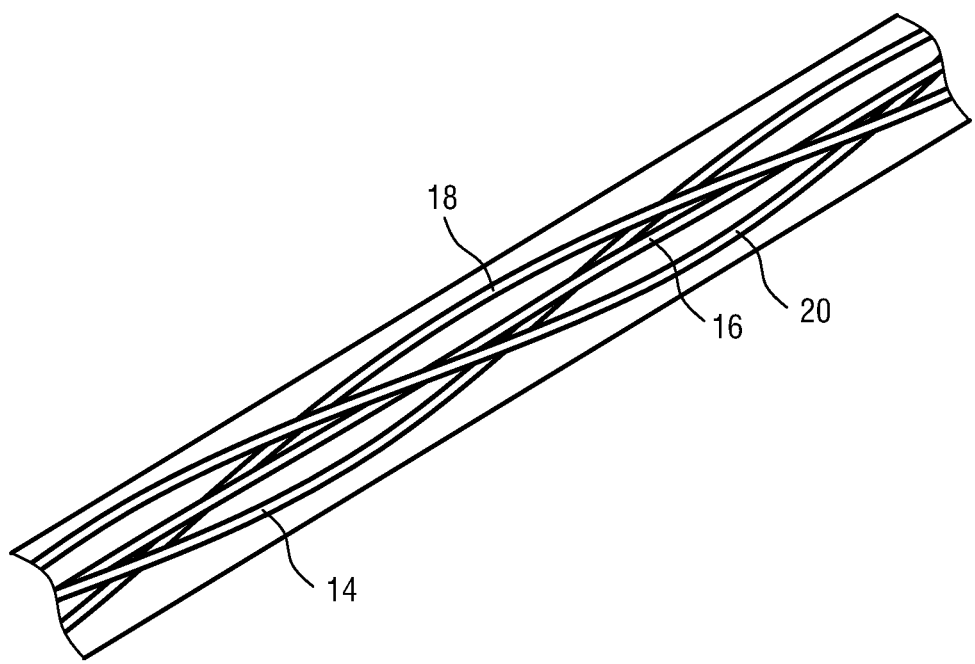
FIG. 2 shows a piece of length of an example of an optical fiber.

FIG. 2 shows a piece of length of the fiber cores 14, 16, 18, 20 with the outer cores 14, 18, 20 spiraled around the center core. The outer cores are angularly spaced with respect to one another around the longitudinal center axis of the optical fiber 12. The center core 16 may be positioned on the longitudinal center axis, with some tolerances due to the fiber manufacturing process. According to a number of four cores with three outer cores in the present example, the angular spacing between neighboring cores typically is 120°.

With reference again to FIG. 1, the FORS system 10 may comprise an optical shape sensing console 21. The optical shape sensing console 21 is also referred to herein as interrogator for optically interrogating the optical fiber 12. The system 10 may be adapted to carry out the method according to the principles of the present disclosure, which will be described below.

The shape sensing console 21 may comprise a tunable light source 22 which can be swept through a range of optical frequencies. The light emitted by the light source 22 is coupled into an optical interferometric network 24 having optical channels 24a, 24b, 24c, 24d. In use of the optical shape sensing system 10, each of the single fiber cores 14, 16, 18, is connected with one of the optical channels 24a, 24b, 24c, 24d.

When the tunable light source 22 is swept through a range of optical frequencies (or wavelengths), each channel 24a, 24b, 24c, 24d, and thus each fiber core 14, 16, 18, 20 of the optical fiber 12 is simultaneously but independently optically interrogated, and the resulting interference pattern from reflected light from each of the fiber cores 24, 26, 28, 20 and reference light is routed to a processing unit 26 via respective photodetectors 25. Each channel 24a, 24b, 24c, 24d may be processed independently from the other channels. The distributed strain measurements recorded using the multiple channel OFDR system from the cores 14, 16, 18, 20 may then be exported for use for further processing, in particular for 3-dimensional shape reconstruction of the fiber sensor 12 and for visual display of the reconstructed 3-dimensional sensor fiber shape, wherein these processings may be performed by a processor or circuitry 27.

The optical fiber 12 may be integrated into a device (not shown). Such a device may be, for example, a guidewire, a catheter, an endoscope or the like.

In OSS, geometrical changes of the optical fiber 12 are encoded into the light field that propagates through the fiber 12. Optical interrogation of the optical fiber 12 gives the information needed to, in principle, reconstruct the 3-dimensional shape of the whole fiber 12, and thus of the device comprising the fiber 12, in real time. Given an appropriate coordinate system or reference frame, it is possible to know the exact orientation and position of the complete fiber 12 in real time.

A more detailed overview about the principles of optical shape sensing can be taken from US 2012/0069347 A1 and U.S. Pat. No. 8,773,650 B2.

Figure 3:
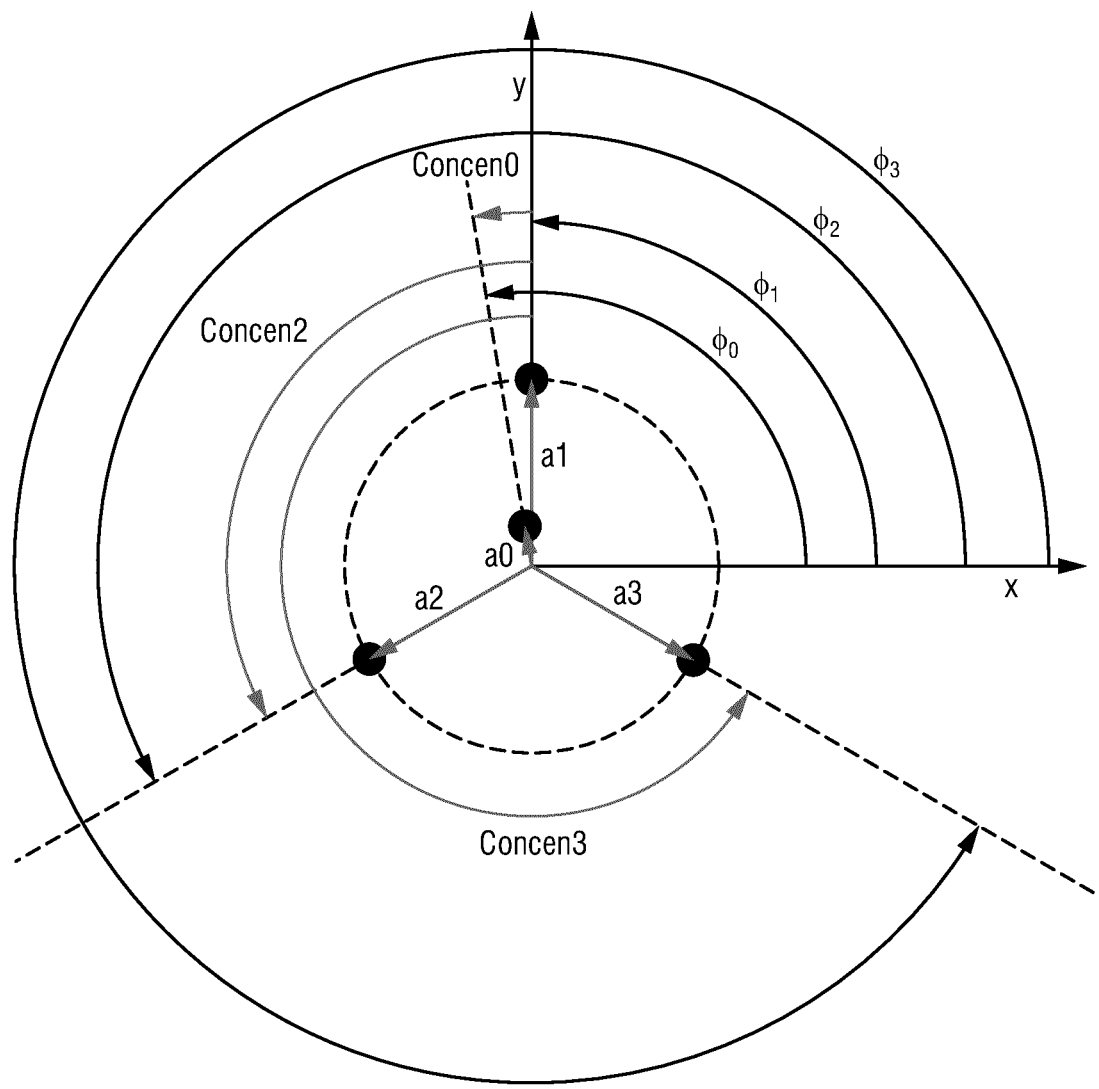
FIG. 3 shows core geometry of a multi-core optical fiber of a typical FORS sensor in a coordinate system with its origin placed on the mechanical center of the fiber.
Figure 5:
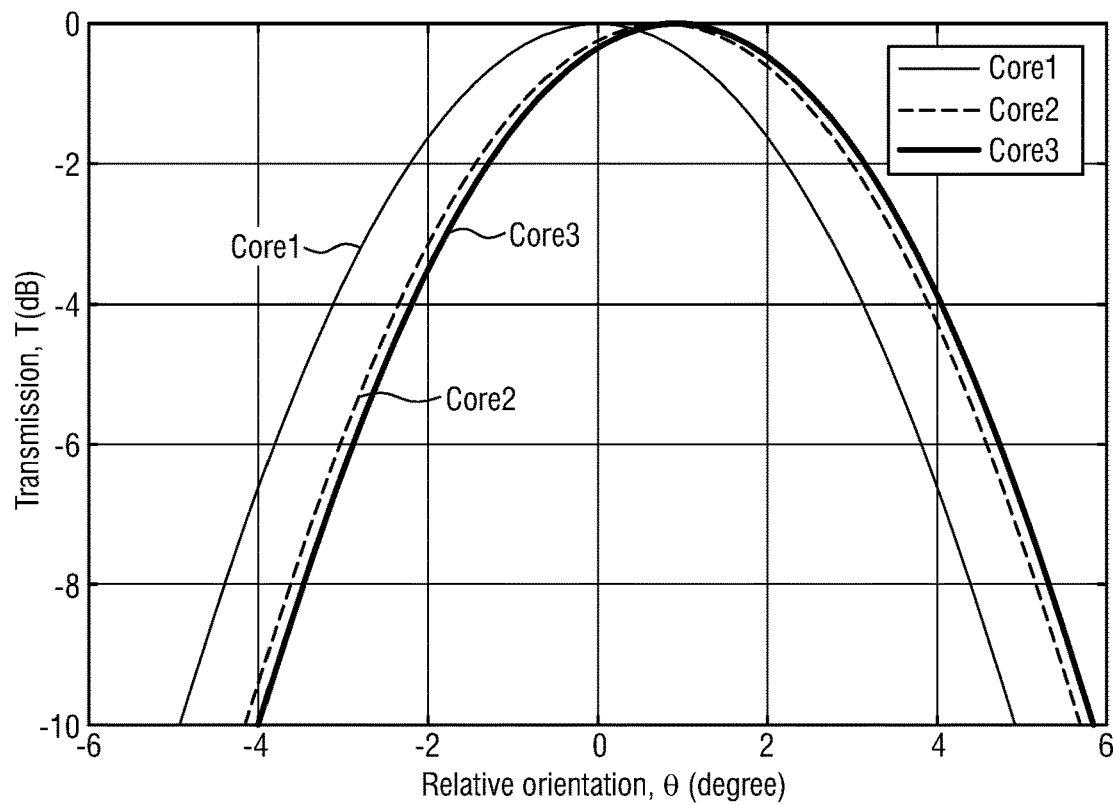
FIG. 5 shows insertion-loss curves of light transmission from a first fiber to a second fiber for each core of the fibers as a function of relative rotational angle between the first and second fibers at a connection position.

FIG. 3 shows the core geometry of a 4-core optical fiber which may be used as or in a FORS sensor, in a coordinate system with its origin placed on the geometrical center of the fiber. In FIG. 5, the number 0 exemplarily denotes the center core, and the numbers 1, 2, 3 exemplarily denote the outer cores. The cores are at an angle $\phi_i$ and a distance $a_i$ (i=0, 1, 2, 3) with respect to the origin of the chosen coordinate system. Relative angles $c_i$ (concens) and relative distances $r_i$ (radials, not shown) with respect to core 1 are defined in FIG. 5. Thus, in more generality, $c_i=\phi_i-\phi_1$ and $r_i=a_i/a_1$, with i=1, 2, ..., N, with N the number of outer cores of the fiber. In this definition, $c_i$ are the relative angles with respect to the angular position of a reference core, here core 1. Similarly, $r_i$ are normalized on the radial distance of core 1 from the center of the fiber.

The nominal values for $c_i$, of the outer cores are $c_i=(i-1)360/N$, i=1, 2, ..., N, and $r_i=1$, if all outer cores have the same radial distance from the fiber center as core 1. In practice, manufacturing tolerances will result in small variations of these nominal values of $c_i$ and $r_i$.

Figure 4:
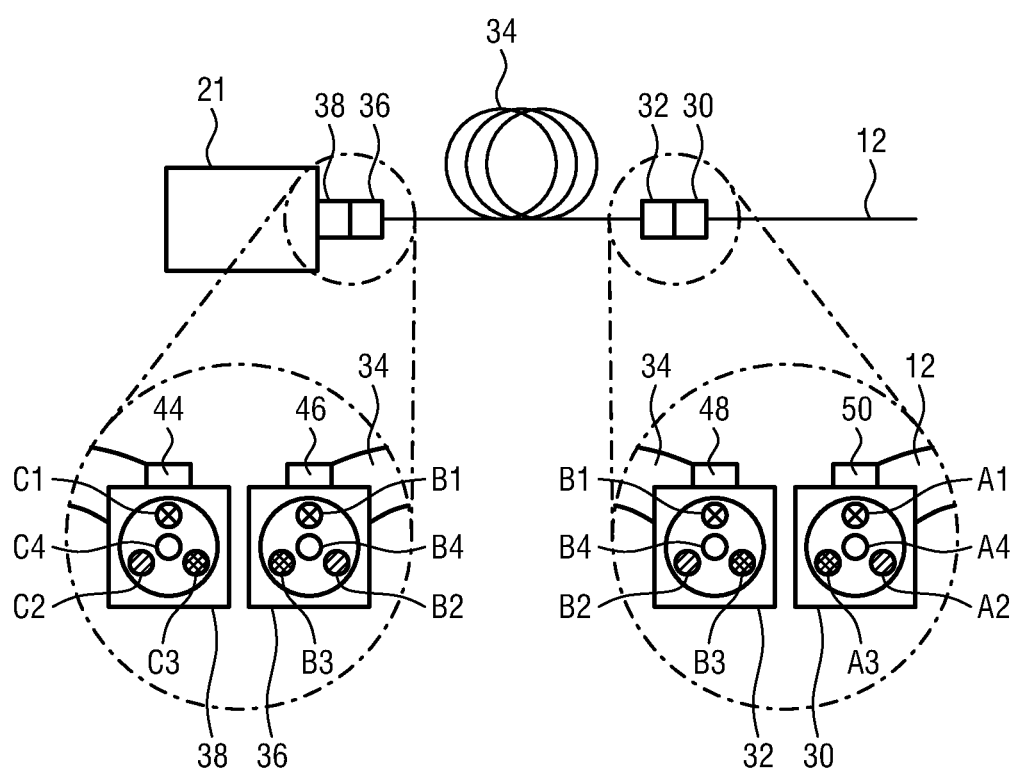
FIG. 4 shows a simplified sketch of the system in FIG. 1 with details thereof enlarged.

FIG. 4 shows a conventional FORS setup, with those elements corresponding to elements in FIG. 1 being labeled with the same reference numerals as in FIG. 1. As such, FIG. 4 shows in simplified manner a shape sensing console or interrogator 21 and an optical fiber 12 connected to the shape sensing console 21. The optical fiber 12 may be connected to the shape sensing console 21 via a patch cord which also is equipped with an optical fiber 34 having the same number of fiber cores as the optical fiber 12. The patch cord is not necessarily present, but the optical fiber 12 could be directly connected to the shape-sensing console 21. In FIG. 4, the fiber cores of the optical fiber 12 are denoted with A1, A2, A3, A4, and fiber cores of the optical fiber 34 of the patch cord are denoted with B1, B2, B3, B4. C1, C2, C3, C4 denote the cores of the optical fiber emerging from the interrogator (shape sensing console 21).

In use of the system 10, an end section of the optical fiber 12 which is equipped with a connector 30 is connected to an end section of the optical fiber 34 of the patch cord which is equipped with a connector 32. Similarly, a proximal end section of the fiber 34 of the patch cord which is equipped with a connector 36 may be connected to an end section of a fiber having the optical channels 24a, 24b, 24c, 24d as cores integrated therein. When the patch cord is not used, the connector 30 having the optical fiber 12 is directly connected to the fiber of the interrogator or shape sensing console 21.

To make a functional optical connection between the optical fiber 12 and the optical interrogator 21 (optionally via the optical patch cord 34), it is important to align the outer cores and the central core of the optical fiber 12 with the outer cores and central core of the fiber 34 of the patch cord or of the interrogation console 21 at the connection position. A common way to achieve such an alignment is to assemble both optical fibers into a kit fiber connector 30, 32 (or 36, and 38) each having a key 48, 50 or 44, 46, respectively, which are configured to mate for locking the connection between the optical fibers in a rotationally fixed standard orientation. Low tolerance elements (not shown) in the connectors 30, 32 (or 36, 38), such as ceramic ferrules, ensure the centering of the two fibers inside a mating sleeve. The connector keys 48, 50 (or 44, 46) define the angular alignment.

For certain designs of guidewires, such as back-loadable guidewires, where the outer diameter typically cannot be larger than a fraction of one mm, a robust connector like key 50 is very difficult to manufacture. In this case, active alignment methods may be needed to ensure the proper optical connection between the outer cores of the connected two optical fibers. Embodiments of such an alignment method will be described herein.

In FORS, the reconstruction algorithms create a shape starting at a certain position on the FORS sensor fiber, which position (starting position) is referred to as the launch of the reconstructed shape (or just launch). When the starting position of the sensor moves either in position (x, y, and z) or in direction ($R_x$, $R_y$, and $R_z$) the whole reconstructed shape translates or rotates with it. To ensure that the reconstructed shape is displayed in a stable way, it is important to always know the position and direction of this starting point with respect to the relevant coordinate system. This can be done by ensuring that this part of the sensor cannot move with respect to the coordinate system (no rotation and no translation) using a mechanical launch fixture, or by constantly measuring the rotation and translation of the starting point and correcting the shape for any movement.

The reconstructed shape can then be displayed in a relevant coordinate system, such as one that matches an operating theatre in which FORS is used, for example linked to a surgery table. It is possible that an additional registration step is required to correctly translate and rotate the shape to the desired position and orientation. Such a registration step can be done by comparing the shape with a ground truth of e.g. an X-ray image. Once this registration is done and as long as the launch position and orientation are stable (or continuously known so that one can correct for any movement), the reconstructed shape of the optical fiber will be correctly shown in the desired coordinate system to which it was matched.

During a medical procedure, FORS guidewires might need to be connected, disconnected, and re-connected several times. This is especially true for back-loadable FORS guidewires for which the conventional way of fixating the launch region cannot be used because there are strict restrictions on the outer diameter of the device. When such a guidewire is disconnected to slide a therapy device over the proximal end of the guidewire, one does not want to need a re-registration during re-connection of the optical fiber of the FORS guidewire with the patch cord (or directly with the interrogator) as this would cause delay in the procedure.

To avoid the need for re-registration, the orientation and position of the optical fiber of the FORS sensor at the connection position at which the optical fiber is connected to the optical fiber of the patch cord or interrogator need to be known with a high accuracy after each re-connect. While for most of the degrees of freedom (x, y, z, $R_x$, $R_y$) mechanical solutions can ensure that the guidewire is reconnected in a reproducible way, the relative rotational angle, i.e. $R_z$, between the two fiber end sections connected at the connection position about the longitudinal axis (which is also referred to as relative roll), is a hard problem for which a mechanical solution cannot provide the required accuracy. For example, for a good optical connection between two multi-core FORS fibers, having outer cores at 35 micron, it is sufficient to align the relative roll between the two fibers within one degree (17.5 mrad) such that the corresponding outer cores of the two fibers overlap within a fraction of a micron. This amount of accuracy is also what conventional mating methods, such as mating sleeves, can provide. However, in order to correctly map the shape of the device with integrated fiber to the relevant coordinate system, the relative roll must be known with an accuracy of at least an order of magnitude higher. An error of 1 mrad can already give 1 mm error over 1 m of reconstructed shape of the device. It is therefore not possible to rely on the fact that once a good optical connection is made upon re-connecting the two fibers that also the relative roll is sufficiently equivalent to the value it was during a previous connection on which registration was based.

According to the principles of the present disclosure, a method of re-connecting a first optical fiber (like optical fiber 12 in FIG. 4) with a second optical fiber (like an optical fiber of patch cord 34 in FIG. 4) avoids a re-registration of the current connection position of the two fibers in that the registered connection position, which has been determined with respect to the relevant coordinate system during a previous connection of the two fibers, may be modified with the current relative roll with respect to the previous or initial connection between the two fibers. The method may make use of an optical measurement of an optical quantity at the current connection position where the fibers are re-connected.

Coupling light from one fiber into another fiber usually results in some loss depending on how well the modes of the fiber cores in the two fibers overlap. This loss, called insertion loss, can be expressed in terms of the transmitted power T. The spatial mode overlap between two nominally equivalent cores is determined by their relative alignment. Assuming that the optical fibers are directly coupled such that there is no gap between them, and that the angular mismatch is small, and that both fibers have the same mode field radius $\omega_0$ (the radius at which the intensity drops to $1/e^2$) at a free space wavelength, the power transmission $T_{ij}$ between core i in the first fiber and core j in the second fiber, in decibels, also referred to as insertion loss, can be expressed as follows:

$$T_{ij}^{dB} = 10 \cdot \log 10(T_{ij}) = -\frac{10 d_{ij}^2}{\omega_0^2 \ln(10)} = -\frac{20 a^2}{\omega_0^2 \ln(10)}(1 - \cos(\delta_{ij} - \theta)). \quad (1)$$

In equation (1), $\omega_0$ is the mode field radius, a is the core distance from the fiber center which is here, to simplify calculation, considered to be the same for all outer cores, $\delta_{ij} = c_i^1 - c_j^2$ being the difference between the concens of core i in the first fiber and concens of core j in the second fiber, and θ is the (unknown) relative rotational angle (roll) about the longitudinal axis between the first fiber and the second fiber upon re-connecting the fibers.

The difference $\delta_{ij}$ is a specific characteristic which is a measure for deviations of angular positions of the outer cores of the first fiber with respect to angular positions of the outer cores of the second fiber which deviations may be caused by tolerances in the manufacturing process of the two optical fibers. $\delta_{ij}$ can be determined by e.g. a measurement as will be described below.

Equation (1) can be further simplified by a Taylor expansion around $\delta_{ij}-\theta=0$, because this will be the relevant range in which the optical signals received from the optical interrogation upon re-connecting the two fibers will be used:

$$T_{ij}^{dB} \approx -\frac{20a^2}{\omega_0^2 \ln(10)} (\delta_{ij} - \theta)^2. \quad (2)$$

The insertion loss $T_{ij}^{dB}$ between core i of the first fiber and core j of the second fiber the connection position can be measured in dependence on the relative rotational angle θ by optically interrogating the two fibers. Different optical techniques can be used to measure the insertion loss, while it might be easiest to use OFDR-like technologies. An OFDR system like system 10 in FIG. 1 allows to measure the reflection in a fiber as a function of position with a high spatial resolution. FORS is relying on OFDR to interrogate reflection patterns in each core of an optical fiber separately and is therefore also capable of measuring insertion losses over an optical connection between two optical fibers.

FIG. 5 shows curves of insertion losses between two optical fibers trough a connection position as function of the relative rotational angle θ for a multi core fiber with N=3 outer cores. The curves in FIG. 5 have been obtained from a simulation. It is to be noted again that the number of outer cores needs to be equal to or larger than two for the present invention to be applicable. In the present simulation, the radial distance of the fiber cores from the fiber center are assumed to be 35 μm, and the outer cores are assumed to be arranged at nominal azimuthal angles with respect to core 1 of −120° and +120°. Further, core angle deviations between the cores of the first fiber and the cores of the second fiber have been taken into account to simulate manufacturing tolerances. It has been assumed that $\delta_{11}=0$, $\delta_{22}=0.014$, and $\delta_{33}=0.016$ rad. The field mode radius $\omega_0$ is set to 2.8 μm.

Figure 6:
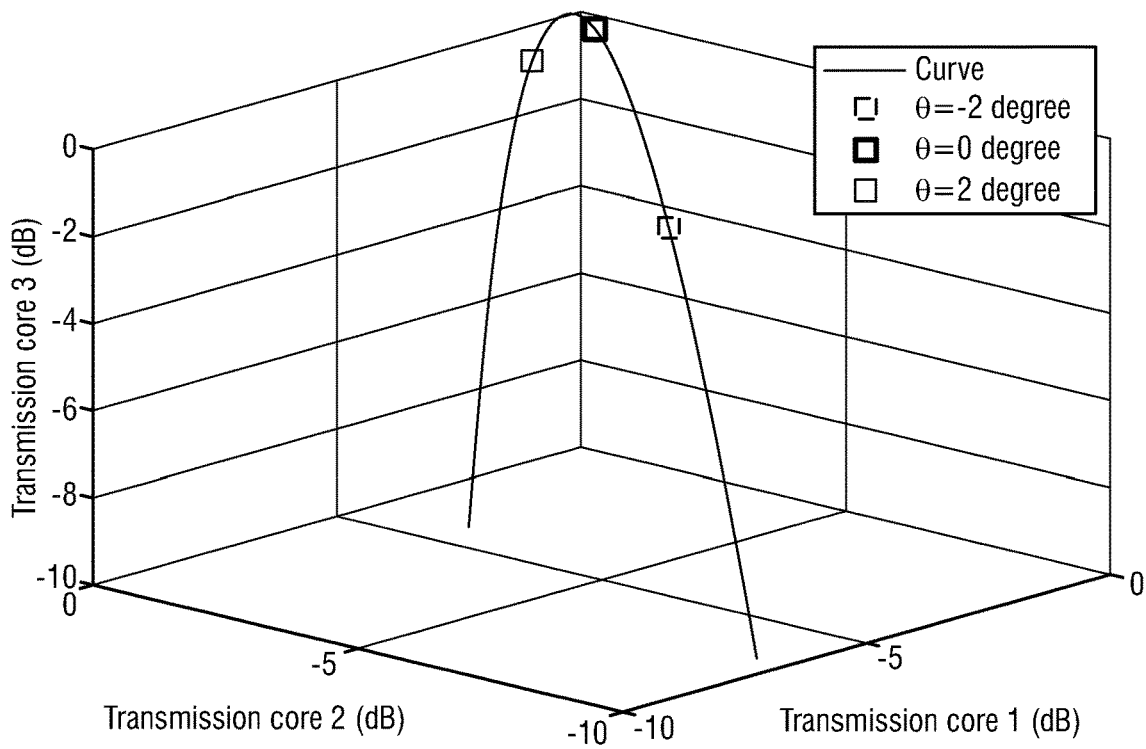
FIG. 6 shows the insertion-loss curves in FIG. 5 combined into a vector and plotted in a 3D-plot.

The insertion losses of all outer cores may be combined into a vector as shown in FIG. 6. This vector traces a curve in a 3-dimensional space as function of the relative rotational angle θ. The difference in geometry of the first fiber and the second fiber will give a distinct relation between the insertion losses of the outer cores. In the example of three outer cores, the vector is 3-dimensional. Analytically, the vector may be described by:

$$\vec{r_1} = -\frac{20a^2}{w_0 \ln(10)} \langle (\delta_{11} - \theta)^2, (\delta_{22} - \theta)^2, (\delta_{33} - \theta)^2 \rangle.$$

For a given fiber design it is possible to assume that $\omega_0$ and a are known. The only unknown parameters are $\delta_{11}$, $\delta_{22}$, and $\delta_{33}$ that depend on the exact geometry of the first optical fiber compared to the second optical fiber. These values can be found from a measurement by, for example, fitting a plane to the points, because the normal vector to the plane, is proportional to:

$$\vec{N} \propto \langle \delta_{22} - \delta_{33}, \delta_{33} - \delta_{11}, \delta_{11} - \delta_{22} \rangle.$$

In the present embodiment, it is assumed that the angular rotational angle θ between the two optical fibers is unknown in the current connection position upon re-connecting the two fibers. It is further assumed in the present embodiment, that after a re-connect of the two fibers, the same cores are connected to each other as in a previous connect, i.e. core 1 of the first fiber is connected to core 1 of the second fiber, core 2 of the first fiber is connected to core 2 of the second fiber, and core 3 of the first fiber is connected to core 3 of the second fiber. This specific core-to-core configuration in which the same cores of the fibers are connected to each other after re-connect as before the re-connect, can be achieved in several ways. For example, this alignment can be achieved by a rough keying mechanism that is good enough to ensure an alignment within 360/N degrees, with N the number of outer cores. Another way to achieve this alignment is to identify during alignment which cores of the first fiber are connected with which cores of the second fiber using an optical finger print, for example as described in WO 2017/182535 A1 and providing a feedback signal to keep rotating when the wrong cores are connected. This would require that the two fibers can be rotated over full 360° with respect to each other.

While it is to be expected to always measure an optical signal for the center core when the two fibers end faces are brought in each other's proximity, as it is in principle not dependent on the relative angular orientation between the two fibers, on the outer cores there is a large chance that the optical signal at first contact between the two fibers is not obtained without any additional active rotational alignment.

After positioning the end sections of the two fibers in proximity so as to be aligned with one another along the longitudinal axis of the end sections in the current connection position including the current connection orientation, in which the current relative rotational angle is unknown, the two fibers (i.e. one of the two fibers or both fibers) are rotated with respect to one another. During rotation, the insertion loss in the outer cores will change. From equation (2) it can be seen that the insertion loss in decibels depends approximately quadratically on the angular mismatch, $\delta_{ij}-\theta$, between the pairs of cores that are mated. The width of the curves in FIG. 5, i.e. how fast the transmission decreases with a certain rotation, is solely given by the nominal core distance from the center, a, and the mode field radius $\omega_0$. The relative position of the curves in FIG. 6 with respect to each other depends on $\delta_{ij}$.

Figure 7:
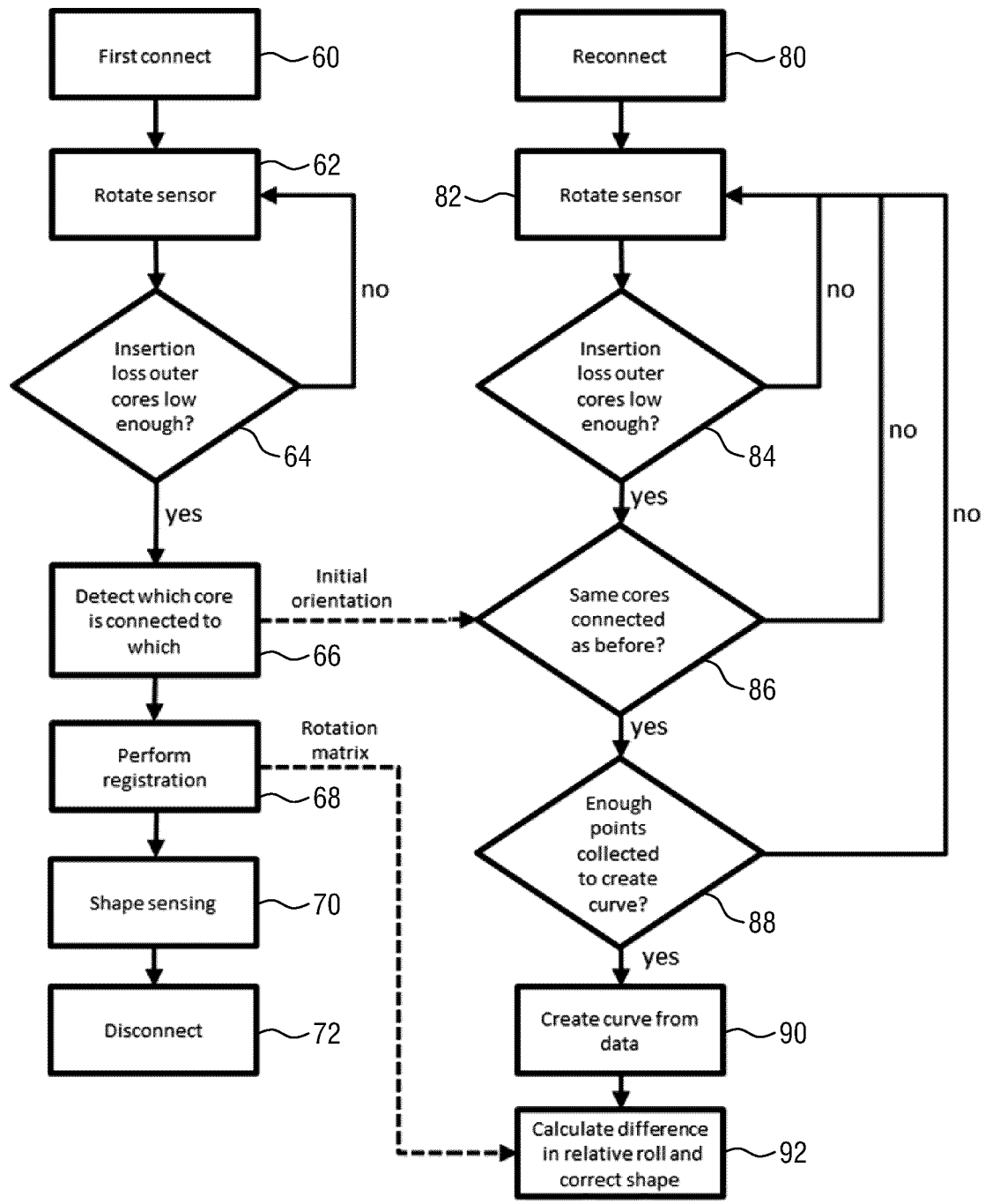
FIG. 7 shows a flowchart of an embodiment of a method of re-connecting two fibers with another according to a first embodiment.

FIG. 7 shows a flow chart describing a possible implementation of a method according to the present embodiment. On the left hand side of FIG. 8, the flow chart describes the steps at an initial or previous connect of the two fibers, and the right-hand side describes the steps of a re-connect of the two fibers after disconnection.

In step 60, the end sections of the two fibers are initially positioned in proximity at a connection position (for example via connectors 30 and 32 in FIG. 4, but without connector key at least on connector 30) so as to be aligned in longitudinal direction of the fibers. In step 62, the end sections are rotated with respect to one another. For example, only the end section of the optical fiber comprised by the FORS sensor is rotated relative to the fixed end section of the other optical fiber, for example of the patch cord. During rotation, the insertion loss is constantly measured on all the outer cores. If, in step 64, it is determined that the insertion loss of the outer cores is not minimum, rotation is continued. If, in step 64, insertion loss reaches minimum, the method proceeds to step 66 where it is detected which core of the first fiber is connected to which core of the second fiber. During measurement of the insertion loss in step 64, enough measurement points are obtained to derive $\delta_{11}$, $\delta_{22}$, and $\delta_{33}$ from the data for the specific core-to-core configuration. $\delta_{11}$, $\delta_{22}$, and $\delta_{33}$ are stored in the memory of the system like system 10. The memory can be comprised by the circuitry 27 of the system 10. Also the point on the curve (FIG. 6) is stored where the alignment stops.

FIG. 6 shows exemplary points on the curve which are denoted corresponding to θ=−2, 0, and 2°.

The method now proceeds to step 68 which is a registration step to match the first and second fibers, including the connection position, in the relevant coordinate system, for example a surgery table in a medical application. Such a registration step can be done by using X-ray imaging, but also by other imaging modalities. From the registration step, a rotation matrix is obtained as known in the art which is then stored in memory. Thus, the registered connection position including connection orientation is the connection position including connection orientation which is registered with respect to the relevant coordinate system upon the initial or previous connect.

Shape sensing can now be performed mapped to the relevant coordinate system to which the fibers are registered, in step 70.

At a certain point in the procedure, the FORS sensor, for example a guidewire, will have to be disconnected from and re-connected to the patch cord or interrogator, for example when a device exchange is needed, as indicated in step 72.

After device exchange, the two optical fibers have to be re-connected. The end sections of the two fibers are again positioned in proximity so as to be aligned with respect to one another in longitudinal direction in a current connection position including a current connection orientation. In the current connection orientation, the relative rotational angle between the first and second end sections of the optical fibers are unknown, or at most known with insufficient accuracy. In step 82, the end sections of the fibers rotated relative to one another about the longitudinal axis to optimize the optical signal received from the outer cores during optical interrogation of the outer cores, until the insertion loss of the outer cores is low enough, as indicated by step 84. In step 86, it is detected if the same cores of the first and second fibers are connected as in the previous connection position. If this is not the case, the system 10 may indicate to the user to further rotate the end section of the first optical fiber with respect to the end section of the second optical fiber until the same cores of the first fiber are connected to the same cores of the second fiber as detected in step 66. Then, insertion losses on the outer cores are again determined. If enough points are collected to create the curve like the curve in FIG. 6 in step 88, the multidimensional transmission curve like the curve in FIG. 6 may be created from the data in step 90. Using the stored characteristic in form of the parameters $\delta_{11}$, $\delta_{22}$, and $\delta_{33}$, together with the known values of the core distance a and the mode field radius $\omega_0$ one can now utilize equation (2) (either by fitting or by inverting the function) to determine the relative rotational angle between the first and second fibers about the longitudinal axis in the current alignment with respect to the registered alignment obtained by the first or previous connect of the two fibers. Thus, the difference in relative roll can be calculated in step 92. When the insertion losses on each of the outer cores can be measured with enough precision, it is possible to find the roll difference with an accuracy of 1 mrad. The reconstructed shape of the optical fiber of the sensor is again rotated using the previously determined rotation matrix (step 68), but on top of that the angular correction based on the calculated relative rotational angle between the two optical fibers is included in the rotation matrix to correct for the roll difference between the first connect and the re-connect.

In the previous embodiment, re-connecting the two fibers includes that the core-to-core configuration after re-connecting the two fibers is the same as the core-to-core configuration in the previous or first connection. In that case, it is sufficient to store the parameters big only for this single core-to-core configuration (e.g. 1-1, 2-2, 3-3). However, it may be desired to limit the rotation of the two fibers with respect to one another, e.g. to minimize the time needed for alignment or reduce the risk of damaging the fiber connector arranged at the end section of the first fiber or of the second fiber. Thus it may happen that upon positioning the end sections at the current connection position in proximity that other cores of the two fibers are mated than in the previous connect. For example, upon re-connecting, core 1 of the first fiber could be connected to core 2 of the second fiber. The data points that are generated by the measured insertion losses on the outer cores will now lie on a different curve compared to the situation before the disconnect, making a direct comparison to find the relative rotational angle not possible or at least difficult. To link the different transmission curves, belonging to different core-to-core configurations, a larger number of insertion loss curves is to be considered. For two optical fibers each having N=3 outer cores, there are three possible core-to-core configurations of the outer cores. Instead of one insertion loss curve as in FIG. 6, there are now three different curves $$\vec{r_1} = -\frac{20a^2}{w_0 \ln(10)} \langle (\delta_{11} - \theta)^2, (\delta_{22} - \theta)^2, (\delta_{33} - \theta)^2 \rangle,$$

$$\vec{r_2} = -\frac{20a^2}{w_0 \ln(10)} \langle (\delta_{12} - \theta)^2, (\delta_{23} - \theta)^2, (\delta_{31} - \theta)^2 \rangle,$$

$$\vec{r_3} = -\frac{20a^2}{w_0 \ln(10)} \langle (\delta_{13} - \theta)^2, (\delta_{21} - \theta)^2, (\delta_{32} - \theta)^2 \rangle.$$

It is to be noted again that this principle can be generalized to any number of outer cores ≥2.

Figure 8:
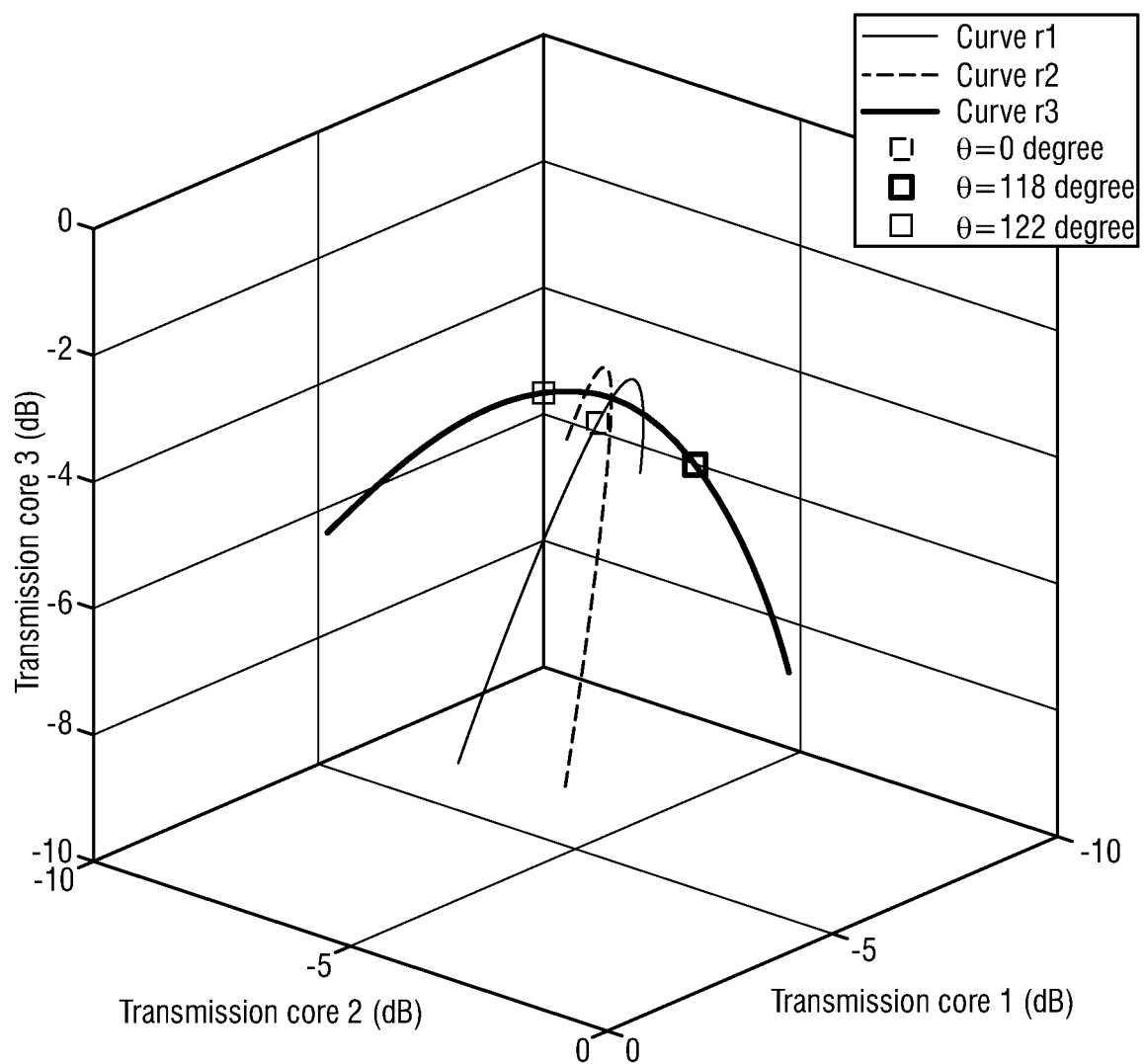
FIG. 8 shows a simulation of insertion-loss curves of light transmission from a first fiber to a second fiber connected with the first fiber as a function of relative rotational angle between the two fibers, wherein all possible core-to-core configurations of the cores of the two fibers are taken into account.

The three vectors indicated above all depend on geometrical differences between the two connected optical fibers. This means that $\delta_{ij}$ should be known for any combinations of i and j. If $\delta_{ij}$ is known for all possible combinations, as well as the nominal outer core distance a and the mode field radius $\omega_0$, the curves for all possible core-to-core configurations can be predicted. These curves are shown in FIG. 8.

A measurement of $\delta_{ij}$ for all core-to-core configurations can be done upfront as a manufacturing step for example the patch cord and the sensor each comprising a specific fiber.

Figure 9:
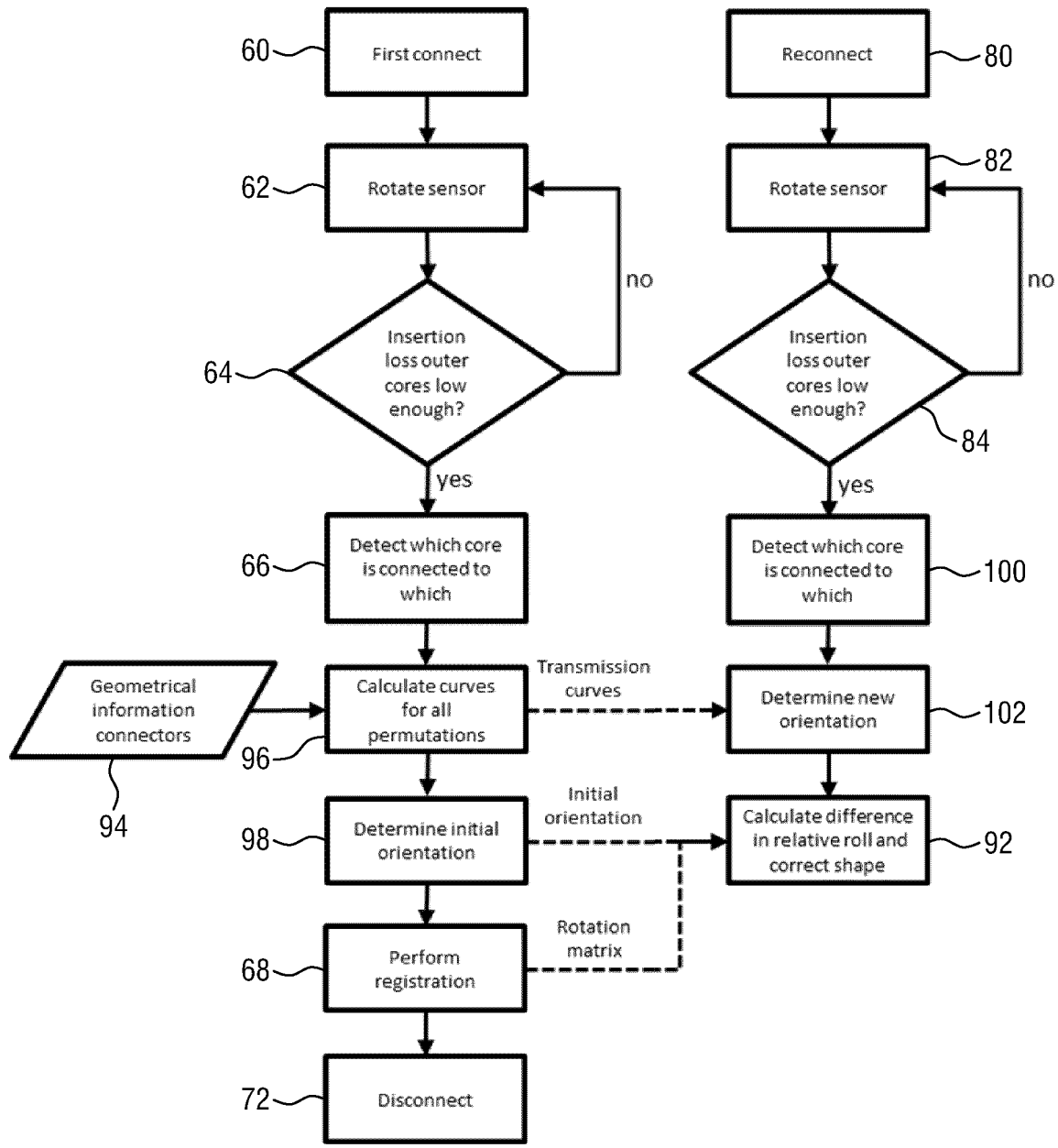
FIG. 9 shows a flowchart of a method of re-connecting two optical fibers to one another according to a second embodiment.

FIG. 9 is a flow chart describing a possible implementation of the present embodiment. Steps 60 to 66 may be the same as in the flow chart of FIG. 7. Using the geometrical information $\delta_{ij}$ on the two optical fibers at their connectors, as indicated in step 94, the transmission curves can be calculated for all permutations of core-to-core alignments in step 96. The established transmission curves will be used in the re-connection of the two fibers.

In step 98, the core-to-core configuration upon the initial or first connect of the two fibers is determined.

Steps 68 and 72 are the same as in the flow chart of FIG. 7.

During re-connect, after steps 80, 82, 84 have been carried out, it is detected, which core of the first fiber is connected to which core of the second fiber in the current connection position, as indicated by step 100. Now, using the transmission curves obtained in step 96, and knowing all these curves allows to determine the location on these curves before and after re-connection. With that knowledge, the relative rotational angle θ can be found for every value of θ between 0 and 360°, as shown in FIG. 8. The new core-to-core configuration can be determined in step 102.

From that and using the transmission curves like the curves in FIG. 8, the value of θ can be found, and this value of θ can then be used in step 104 to correct the rotation matrix obtained in the registration step 68.

As described with respect to the embodiments above, the insertion losses of the outer cores in the optical fiber of a FORS sensor can be combined into a vector, for example as shown in FIGS. 6 and 8, that traces a curve in a N-dimensional space, with N being the number of outer cores. Now, it is possible to take the actual or current position on the curve as a feedback signal upon re-connecting the two fibers, as this signal has information on which side of the optimum (e.g. maximum transmission) the current alignment is. Hence, it is now possible to give to the user directional information during the alignment.

Figure 10:
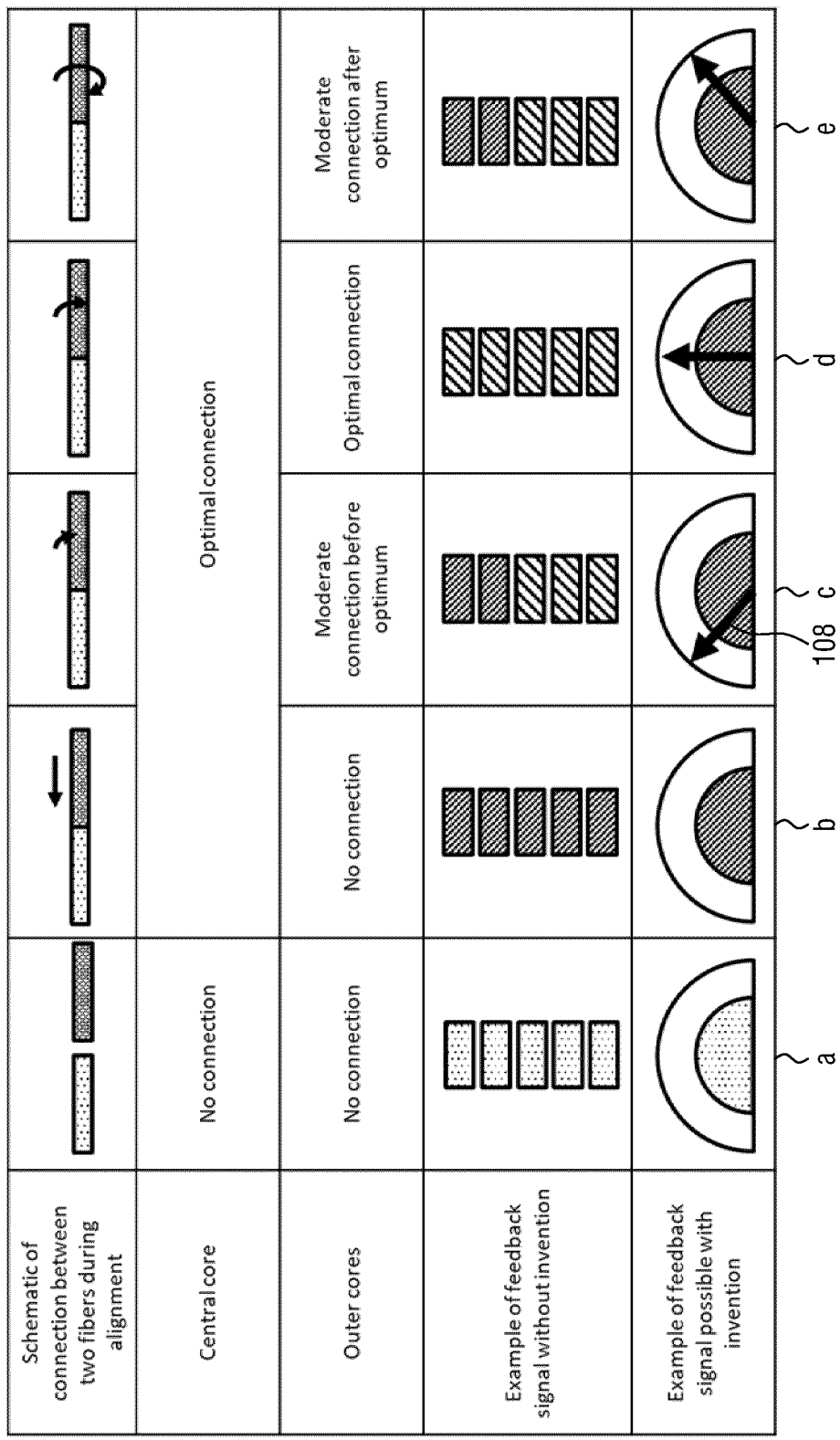
FIG. 10 shows a sketch of examples of possible feedback to a user without and with implementation of the present invention at different stages of alignment of two optical fibers with respect to one another.
Figure 11:
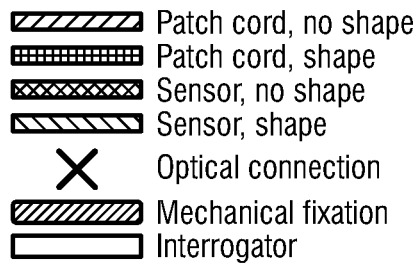
FIG. 11 a) to c) show sketches of three possible configurations of a FORS setup including an interrogator, a patch cord equipped with a multicore optical fiber, a sensor equipped with a multicore fiber, and a launch region, wherein FIG. 11a) shows a conventional setup, and FIGS. 11b) and 11c) show embodiments of a setup using the present invention.
Figure 11:
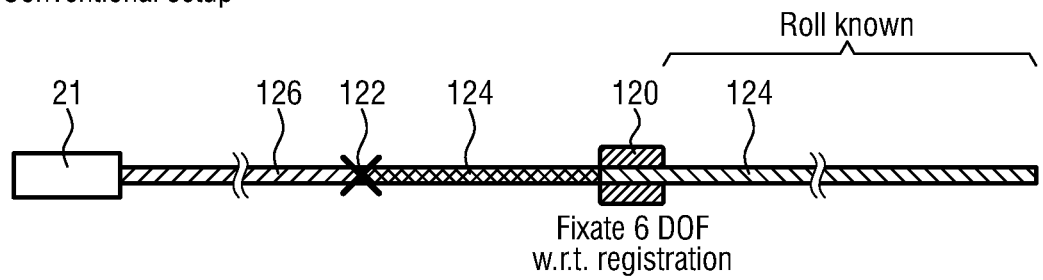
Figure 11:
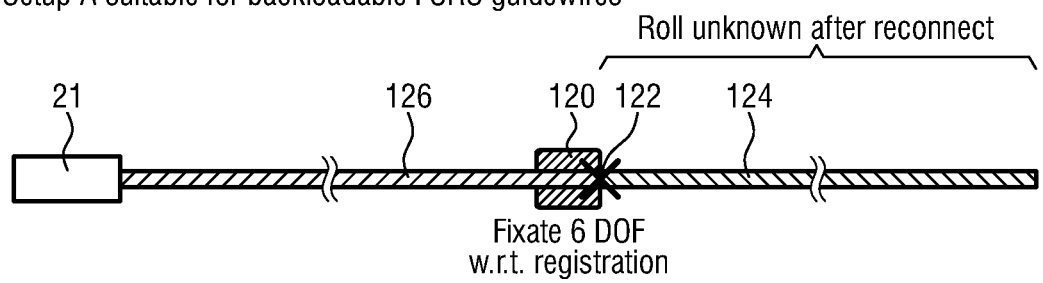
Figure 11:
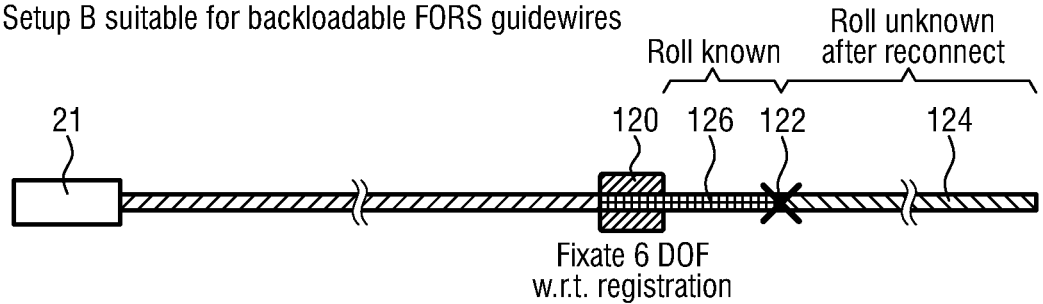

This is illustrated in FIG. 10. FIG. 10 shows several steps (a) to (e) during the alignment of an optical fiber of a FORS sensor. For each step (a) to (e), it is indicated in FIG. 11, what a conventional feedback signal could look like and what it could look like using the principles of the present disclosure. By examining the central core of the optical fiber of the sensor, the system can (only) determine whether a sensor is connected or not (step (a) and (b)). Then a rotational alignment is done to align the outer cores (steps (c), (d), (e)). Without the principles of the present disclosure, it is not possible to see whether the rotational alignment about the longitudinal axis is before or after the optimum, while with the invention it is possible to discriminate between these alignments, as shown by an indicator 108. Indicator 108 may be visually displayed by the system, for example on a graphical user interface. Instead of a visual indicator, it is also feasible that an audio signal is output as the indicator, wherein a direction may be indicated by a certain frequency and/or loudness.

With reference to FIG. 11, implementation of the principles of the present disclosure in a FORS system, like system 10, will be further described.

FIG. 11a) shows a conventional setup. In conventional setups, a mechanical launch fixture 120 and start of the shape reconstruction distal from the optical connection 122 of the optical fiber of the sensor 124 to the optical fiber of the patch cord 126 (or directly to the interrogator 21) is defined distally from the optical connection 122, as shown in FIG. 11a). Thus, throughout the full reconstructed shape of the sensor 124, the twist is continuous. In such a configuration, it is possible to connect and disconnect the sensor 124, while the launch 120 can stay in the mechanically stable launch fixture.

In the use of a back-loadable guidewire as the sensor 124, the setup in FIG. 11a) will not be feasible. That is because the strict dimensional requirements on the outer diameter of the guidewire prevent a robust mechanical launch fixture that can accurately reproduce the relative rotational angle between the end sections of the optical fiber of the sensor 124 with respect to the end section of the optical fiber of the patch cord 126. The x-, y-, and z-position and the orientations of the connectors about the x- and the y-axis can still be mechanically defined.

In FIGS. 11b) and c) two embodiments of possible setups are depicted for use with a back-loadable FORS guidewire as the sensor 124 when implementing the principles of the present disclosure. In FIGS. 11b) and c), the roll (rotational angle about the longitudinal axis) with respect to the registration is fixated proximal from the optical connection 122, which allows to freely disconnect a back-loadable FORS guidewire with an integrated optical fiber from the rest of the system. As the launch fixture 120 is now positioned proximal from the optical connection 122 between the sensor 124 and the patch cord 126, the rotational orientation (roll) of the sensor 124 with respect to the initial registration (via the launch 120) is a priori unknown after a re-connect of the sensor 124. At this point, the principles of the present disclosure as described herein allow to find the relative rotational angle ($R_z$) between the sensor 124 and the patch cord 126 about the longitudinal axis. When this relative rotational angle is known, the shape can be reconstructed with respect to the original registration that was done before the re-connection of the two fibers of the sensor and the patch cord.

The difference between the setups in FIGS. 11b) and c) is that in FIG. 11b) the optical connection 122 is directly at the point where the roll is fixated (mechanical launch). In FIG. 11c), the optical connection 122 is positioned in a distance distally from the fixation 120. The latter setup requires that the shape of part of the patch cord 126 leading from the launch 120 to the optical connection 122 is also reconstructed in order to know the orientation of the patch cord 126 at the connection point 122.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

All registration data, initial or modified ones, or any other optically-based, geometrical or positioning data can be stored, for example in memory or another storage medium.

Any reference signs in the claims should not be construed as limiting the scope.

The invention claimed is:

1. A method of re-connecting a first optical fiber (12) with a second optical fiber, the method comprising:
positioning a first end section of the first fiber and a second end section of the second fiber in proximity so as to be aligned with one another along a longitudinal axis of the first and second end sections in a current connection position including a current connection orientation, in which a current relative rotational angle between the first and second end sections about the longitudinal axis is not known with respect to a relative rotational angle between the first and second end sections in a registered connection orientation which has been determined with respect to a coordinate system during a previous connection of the first fiber with the second fiber, the first fiber and the second fiber each having a plurality of outer cores, optically interrogating the outer cores of the first and second fibers through the current connection position to receive optical signals from the outer cores, and modifying, from the optical interrogation of the outer cores, the registered connection orientation such that the first and second fibers in the current connection orientation including the current relative rotational angle between the first and second end sections about the longitudinal axis are correctly registered with respect to the coordinate system.

2. The method of claim 1, further comprising: indicating to a user a direction in which the first and second end sections are to be rotated with respect to one another about the longitudinal axis for increasing intensity of the received signals to an optimum.

3. The method of claim 1, further comprising:
determining, from the optical interrogation of the outer cores, the current relative rotational angle between the first and second end sections and correcting the registered connection orientation with the determined current relative rotational angle.

4. The method of claim 1, further comprising:
deriving, from the optical signals, an optical quantity chosen from the group consisting of insertion loss, transmission, reflection, at the current connection position for each of the outer cores.

5. The method of claim 4, further comprising:
determining, from the optical quantity for each core, the current relative rotational angle (θ) between the first and second end sections based on a stored characteristic specific of the two fibers to be re-connected.

6. The method of claim 5, wherein the stored characteristic includes deviations of angular positions of the outer cores of the first fiber with respect to angular positions of the outer cores of the second fiber.

7. The method of claim 5, wherein the stored characteristic is determined from an optical measurement of the optical quantity for a plurality of relative rotational angles between the first and second end sections during an initial or previous connection of the first fiber with the second fiber.

8. The method of claim 6, wherein the stored characteristic includes deviations between the angular positions of the outer cores of the first fiber and the angular positions of the outer cores of the second fiber for a combination of the outer cores of the first fiber with the outer cores of the second fiber which have been in optical communication during the previous connection.

9. The method of claim 6, wherein the stored characteristic includes deviations between the angular positions of the outer cores of the first fiber and the angular positions of the outer cores of the second fiber for all possible combinations of the outer cores of the first fiber with the outer cores of the second fiber.

10. The method of claim 1, further comprising:
identifying the current combination of the outer cores of the first fiber with the outer cores of the second fiber.

11. The method of claim 10, further comprising:
indicating to a user to rotate the end sections of the first and second fibers relative to one another about the longitudinal axis until the same cores of the first and second fibers are optically connected with one another as in the previous connection of the first fiber with the second fiber.

12. The method of claim 1, wherein the registered position including the registered orientation is registered with respect to a launch position, and the second fiber is being connected with the first fiber directly at or in a distance distally from the launch position.

13. The method of claim 1, wherein one of the first and second fibers is integrated in a device, the method further comprising reconstructing shape of the device using the registered position modified upon re-connection of the first and second fibers.

14. A system, comprising
a first optical fiber and a second optical fiber, the first fiber and the second fiber each having a plurality of outer cores, a first end section of the first fiber and a second end section of the second fiber positioned with a first end section of the first fiber and a second end section of the second fiber aligned with one another along a longitudinal axis of the first and second end sections in a current connection position including a current connection orientation, in which a current relative rotational angle between the first and second end sections about the longitudinal axis is not known with respect to a relative rotational angle between the first and second end sections in a registered connection orientation which has been determined with respect to a coordinate system during a previous connection of the first fiber with the second fiber, an optical interrogator configured to interrogate the outer cores of the first and second fibers through the current connection position to receive optical signals from the outer cores, and circuitry configured to modify, from the optical interrogation of the outer cores, the registered connection orientation such that the first and second fibers are correctly registered with respect to the coordinate system in the current connection orientation including the current relative rotational angle between the first and second end sections about the longitudinal axis.

15. A non-transitory computer-readable storage medium having stored a computer program comprising instructions, which, when executed by a processor, cause the processor to:

control positioning of a first end section of the first fiber and a second end section of the second fiber in proximity so as to be aligned with one another along a longitudinal axis of the first and second end sections in a current connection position including a current connection orientation, in which a current relative rotational angle between the first and second end sections about the longitudinal axis is not known with respect to a relative rotational angle between the first and second end sections in a registered connection orientation which has been determined with respect to a coordinate system during a previous connection of the first fiber with the second fiber, the first fiber and the second fiber each having a plurality of outer cores, optically interrogate the outer cores of the first and second fibers through the current connection position to receive optical signals from the outer cores, and modify, from the optical interrogation of the outer cores, the registered connection orientation such that the first and second fibers in the current connection orientation including the current relative rotational angle between the first and second end sections about the longitudinal axis are correctly registered with respect to the coordinate system.

* * * * *